(12) United States Patent
Dai et al.

(10) Patent No.: US 11,193,104 B2
(45) Date of Patent: Dec. 7, 2021

(54) SYSTEM FOR HIGH-VALUE UTILIZATION OF ORGANIC SOLID WASTE

(71) Applicant: TONGJI UNIVERSITY, Shanghai (CN)

(72) Inventors: Xiaohu Dai, Shanghai (CN); Yu Hua, Shanghai (CN); Shuxian Chen, Shanghai (CN); Huiping Li, Shanghai (CN); Chen Cai, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 0 days.

(21) Appl. No.: 17/144,998

(22) Filed: Jan. 8, 2021

(65) Prior Publication Data
US 2021/0207074 A1 Jul. 8, 2021

(30) Foreign Application Priority Data
Jan. 8, 2020 (CN) .......................... 202010019077.9

(51) Int. Cl.
*C12M 1/00* (2006.01)
*B01D 3/14* (2006.01)
(Continued)

(52) U.S. Cl.
CPC ............ *C12M 47/18* (2013.01); *B01D 3/143* (2013.01); *B01D 53/1475* (2013.01);
(Continued)

(58) Field of Classification Search
CPC ...... C12M 47/18; C12M 21/04; C12M 23/36; C12M 41/00; B01D 3/143; B01D 53/1475; B01D 53/1493; B01D 53/261; B01D 2252/20484; C10L 3/103; C10L 3/104; C10L 3/106; C10L 2200/0469; C10L 2290/06; C10L 2290/08; C10L 2290/24; C10L 2290/26; C10L 2290/541;
(Continued)

(56) References Cited

FOREIGN PATENT DOCUMENTS

CN 102068890 A 5/2011
CN 203007263 U 6/2013
(Continued)

OTHER PUBLICATIONS

Zhou Tao; Process for Preparing Highly Purified Methane from Liquefied Natural Gas; Dec. 31, 2016; Hang Zhou Kaide Air Separation Plant Co.Ltd.; Zhejiang 311100, China.

*Primary Examiner* — Anita Nassiri-Motlagh

(57) ABSTRACT

A system for high-value utilization of organic solid waste includes an anaerobic digestion unit, a biogas measurement and collection unit and a methane purification and liquefaction unit. The anaerobic digestion unit includes an organic solid waste pretreatment system and an anaerobic digestion device. The biogas measurement and collection unit includes a gas flow meter and a high-pressure biogas collection device. The methane purification and liquefaction unit includes a high-pressure separation tank, a liquefaction pretreatment system, a heavy hydrocarbon and benzene removal device, a two-stage rectification system, a low-temperature pressure liquid storage tank device and a buffer storage tank. The organic solid waste undergoes an anaerobic digestion treatment to produce methane followed by collection, purification and liquefaction.

2 Claims, 1 Drawing Sheet

(51) Int. Cl.
  B01D 53/14    (2006.01)
  C12M 1/34     (2006.01)
  C02F 11/04    (2006.01)
  B01D 53/26    (2006.01)
  C10L 3/10     (2006.01)
  C12M 1/107    (2006.01)
  C12P 5/02     (2006.01)

(52) U.S. Cl.
  CPC ....... *B01D 53/1493* (2013.01); *B01D 53/261* (2013.01); *C10L 3/103* (2013.01); *C10L 3/104* (2013.01); *C10L 3/106* (2013.01); *C12M 21/04* (2013.01); *C12M 23/36* (2013.01); *C12M 41/00* (2013.01); *C12P 5/023* (2013.01); *B01D 2252/20484* (2013.01); *C02F 11/04* (2013.01); *C02F 2209/02* (2013.01); *C02F 2209/06* (2013.01); *C02F 2209/38* (2013.01); *C10L 2200/0469* (2013.01); *C10L 2290/06* (2013.01); *C10L 2290/08* (2013.01); *C10L 2290/24* (2013.01); *C10L 2290/26* (2013.01); *C10L 2290/541* (2013.01); *C10L 2290/542* (2013.01); *C10L 2290/543* (2013.01); *C10L 2290/546* (2013.01)

(58) Field of Classification Search
  CPC ......... C10L 2290/542; C10L 2290/543; C10L 2290/546; C12P 5/023; C02F 2209/06; C02F 2209/38
  USPC ........................................................ 435/167
  See application file for complete search history.

(56) References Cited

FOREIGN PATENT DOCUMENTS

| | | | |
|---|---|---|---|
| CN | 203128553 U | 8/2013 | |
| CN | 108315254 A | 7/2018 | |
| CN | 208328025 U | 1/2019 | |
| WO | WO-2019102364 A1 * | 5/2019 | ............ C12M 21/04 |

* cited by examiner

SYSTEM FOR HIGH-VALUE UTILIZATION OF ORGANIC SOLID WASTE

CROSS-REFERENCE TO RELATED APPLICATIONS

This application claims the benefit of priority from Chinese Patent Application No. 202010019077.9, filed on Jan. 8, 2020. The content of the aforementioned application, including any intervening amendments thereto, is incorporated herein by reference in its entirety.

TECHNICAL FIELD

The present application relates to anaerobic digestion of organic solid waste, and more particularly to a system for high-value utilization of organic solid waste.

BACKGROUND

China is a major producer of organic solid waste. Currently, the organic solid waste is mainly originated from the domestic source (including urban sludge, domestic garbage and garden waste), the agricultural source (including straw, mulch film and livestock and poultry manure) and the industrial source (including oil sludge, bacteria residue and industrial organic solid waste). More than 6 billion tons of the organic solid waste from these three sources exceeds are produced every year, which accounts for more than 60% of the total solid waste generated in China. However, a scientific and reasonable management and safe treatment technology system has not yet formed. Organic solid waste contains many harmful materials with complex components to cause pollution in the case of mismanagement. Currently, organic solid waste generally occupies large area and leads to the formation of combined cross-contamination to the surrounding environment among multiphase interfaces, in addition, it is extremely complex to control such contamination, so mass incidents occur frequently.

Considering that the organic solid waste has a high organic matter content and corruption easily occurs therein, the anaerobic digestion technique displays obvious advantages in the treatment of organic solid waste. Anaerobic digestion can not only reduce the organic solid waste, but also realize the resource utilization of the organic solid waste, which can bring benefits in energy, environmental protection and ecology aspects. The use of organic matter can produce a high-value clean energy, i.e., methane, through digestion by anaerobic microorganisms in the absence of oxygen. The heat of combustion of methane is 802.3 kJ/mol, which makes it an ideal fuel. Currently, methane is mainly produced from the decomposition of organic waste. However, the purity of methane in biogas produced by anaerobic digestion is only 50%-70%, so the methane in biogas has a low degree in high value utilization and is mostly used as domestic energy, for example, it is used for power generation, boiler burning and production heating. In addition, it can also be used as chemical raw materials. The existing techniques for preparing high-purity methane are continuously improved, mainly including a two-stage rectification method, an adsorption-expansion method and an adsorption-batch rectification method, by which the purity of the methane can reach 99.999% or more, which can meet the demand for high purity methane in certain industries.

With the establishment of the low-orbit satellite system by commercial enterprises, the batch launch of satellites is underway. In carrier rockets, liquid rocket engines have many advantages compared to solid engines. Currently, international mainstream and reusable rocket power systems all adopt the liquid rocket engines. In the liquid engines, liquid oxygen hydrocarbon engines, as an important type of rocket engine, are non-toxic and have a higher average density and relatively higher performance. In the liquid oxygen hydrocarbon engines, the liquid oxygen methane rocket engine uses methane as a propellant and liquid oxygen as a combustion-supporting agent. Methane and liquid oxygen are atomized in a certain ratio and then enter the combustion chamber to release a huge driving force after full combustion. Compared to four common liquid oxygen hydrocarbon engines which are prepared from liquid oxygen ethane, liquid oxygen propane, liquid oxygen kerosene and liquid oxygen liquid hydrogen, the liquid oxygen methane engine has relatively higher specific impulse (369 s), low cost, less carbon deposition, non-coking and good cooling performance and can be activated in orbit multiple times, stored for a long time and suitable for repeated use. In addition, the methane has a unique advantage, that is, it can be prepared on other planets, which can be considered as one of future development directions of space propulsion systems, so the liquid oxygen methane engines are researched worldwide, in these researches, it remains to be solved for the source of methane fuel.

SUMMARY

The present application provides a system for high-value utilization of organic solid waste, so as to realize the treatment and disposal of the organic solid waste, solve the problems that a main product of anaerobic digestion, i.e., methane, lacks high-value utilization and handle the fuel source for liquid oxygen methane rocket engines.

In a first aspect, the present application provides a system for high-value utilization of organic solid waste, which includes an anaerobic digestion unit, a biogas measurement and collection unit and a methane purification and liquefaction unit.

The anaerobic digestion unit includes an organic solid waste pretreatment device, an anaerobic digestion device and a residue collection tank which are connected in sequence.

The biogas measurement and collection unit includes a gas flow meter and a high-pressure biogas collection device which are connected in sequence.

The methane purification and liquefaction unit includes a high-pressure separation tank, a liquefaction pretreatment device, a heavy hydrocarbon and benzene removal device, a two-stage rectification device and a low-temperature pressure liquid storage tank which are connected in sequence. The two-stage rectification device is also connected to a buffer storage tank. The buffer storage tank and the low-temperature pressure liquid storage tank are connected.

A gas outlet of the anaerobic digestion device is communicated with a gas inlet of the gas flow meter.

A gas outlet of the high-pressure biogas collection device is communicated with a gas inlet of the high-pressure separation tank.

A liquid outlet of the high-pressure separation tank is connected to a liquid inlet of the two-stage rectification device.

In an embodiment, the anaerobic digestion device includes an anaerobic digestion tank, a heating device and a stirring device. The stirring device is provided in a center of an interior of the anaerobic digestion tank. An outside of the anaerobic digestion tank is surrounded by the heating device. A top of the anaerobic digestion tank is provided with a biogas outlet, a solid material inlet, an acid liquor inlet, an alkali liquor inlet, a pH or temperature detector and a stirring motor. A bottom of the anaerobic digestion tank is provided with a discharge port.

In an embodiment, the heating device is a water-bath heater, a coil heater or a combination thereof.

In an embodiment, the stirring device is selected from at least one of a center shaft mixer, a horizontal mixer, an inclined mixer and a submersible mixer.

In an embodiment, the two-stage rectification device includes a first-stage rectification tower, a two-stage rectification tower, a main heat exchanger, a supercooler, a tower kettle and a tower overhead device which are connected. Their connection manner is similar to that in the existing two-stage rectification process for producing high-purity methane.

In a second aspect, the present application provides a method for high-value utilization of the organic solid waste using the system mentioned above. The method includes the following steps.

The organic solid waste is pretreated by the organic solid waste pretreatment device to obtain a digestion material. Then, anaerobic digestion processes after the digestion material enters the anaerobic digestion device. A biodegradable organic matter in the organic solid waste generates monomers (including monosaccharides, a small amount of amino acids and high fatty acids) under the action of hydrolysis bacteria. The monomers are used to generate an intermediate product, i.e., a volatile organic acid, under the action of acidifying bacteria in the acid production process. In the subsequent process of hydrogen production and acetic acid production, gases (including $CH_4$, $H_2$, $CO_2$ and $N_2$), acetic acid, methylamine and the like are generated. Next, under the action of methanogens, anaerobic digestion products (including digestion residues and biogas) are generated. The biogas generated in the anaerobic digestion unit flows into the gas flow meter of the biogas measurement and collection unit and is converted into a high-pressure raw gas by the high-pressure biogas collection device. The obtained high-pressure raw gas is sent to the high-pressure separation tank to carry out liquid separation treatment to obtain a condensed liquid. The obtained condensed liquid enters into a two-stage rectification system. The high-pressure raw gas enters the liquefaction pretreatment device for desulfurization, dehydration and $CO_2$ removal, and then enters the heavy hydrocarbon and benzene removal device to remove heavy hydrocarbons and trace benzene, and then passes through the two-stage rectification device to generate liquid methane, which is stored in low-temperature pressure liquid storage tank. A small amount of a surplus liquid that undergoes supercooling is discharged into the buffer storage tank for accumulation, and the surplus liquid accumulated to a certain amount is taken out and sent into the low-temperature pressure liquid storage tank.

The non-biodegradable organic matter in the organic solid waste becomes digestion residue through anaerobic digestion and enters a residue collection tank for recycling.

In an embodiment, the digestion material stays in the anaerobic digestion device for 20-40 days.

In an embodiment, a temperature of the anaerobic digestion device ranges within 35-39° C., 41-45° C., or 53-57° C. for biogas production.

In an embodiment, after a pressure of biogas collected in the high-pressure biogas collection device reaches 120 bar at 27° C., the biogas enters the high-pressure separation tank.

In an embodiment, in the liquefaction pretreatment device, $CO_2$ removal, desulfurization and dehydration are carried out. The dehydration is performed after the $CO_2$ removal. The $CO_2$ removal and the desulfurization are simultaneously performed. $CO_2$ is removed by ethanolamine (MEA) through absorption. The dehydration is performed using a molecular sieve dehydration method for further removing sulfide.

In an embodiment, the organic solid waste is one or more combinations of domestic, agricultural and industrial waste.

In an embodiment, the domestic waste is originated from urban sludge, household garbage or garden waste. The agricultural waste is originated from agricultural straw, mulching film, or livestock and poultry manure. The industrial waste is originated from oil sludge, bacterial residue or industrial organic solid waste.

In a third aspect, the present application provides liquid methane produced by the above-mentioned method for use in a liquid rocket engine fuel.

Compared to the prior art, the present application has the following beneficial effects.

Organic solid waste is pressurized and heated for pretreatment, which can destroy colloidal substances, convert macromolecular substances into small molecular substances and convert some organic matters that are hard to be degraded into soluble and easily degradable organic matters, which greatly improves the biodegradability and dehydration performance of the organic solid waste. In addition, the presence of heavy hydrocarbons and benzene in the gas will cause freezing and blockage of a heat exchanger in the two-stage rectification device in a low temperature environment, so there is a need to remove the heavy hydrocarbons and benzene in the gas.

In the present application, based on the anaerobic digestion technique and the methane purification and liquefaction technique, the methane in the biogas produced by anaerobic digestion is purified to a high level, specifically, the purity of the liquid methane after the treatment of the two-stage rectification system is 99.9% or higher. In addition, the purified methane is stored in liquid form, which can meet the demand of liquid oxygen methane engines for methane fuel, thereby achieving high-value utilization of the organic solid waste, augmenting the treatment value of the organic solid waste and solving the problem of low utilization of anaerobic digestion products.

The organic solid waste of the present application is raw materials with wide sources, involves mature treatment techniques, convenient operation and maintenance, and high degree of automation. It can not only solve the problem of safe and systematic disposal of the organic solid waste, but also promote the research and the use of liquid rocket engines, so as to realize green energy supply.

Figure 1:
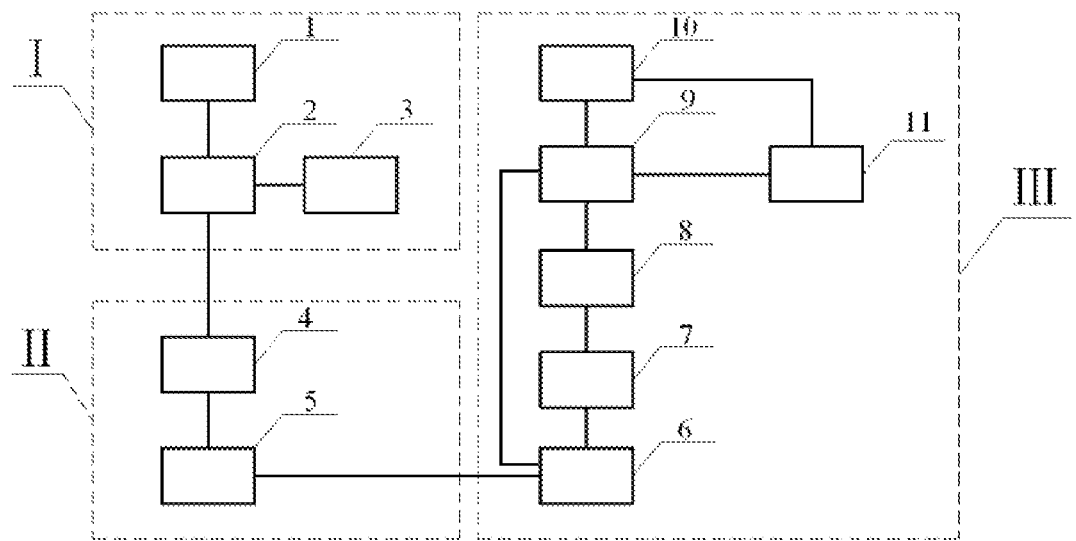
FIG. 1 is a schematic diagram of a system for high-value utilization of organic solid waste according to the present application.
Figure 2:
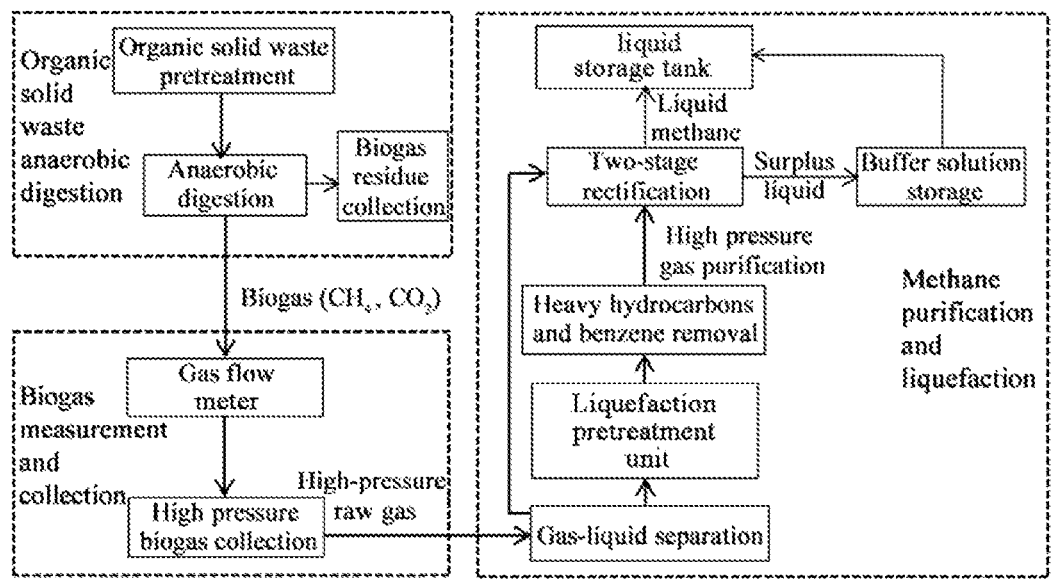
FIG. 2 is a flow chart of a method for high-value utilization of organic solid waste In the drawings: I, anaerobic digestion unit; where 1, organic solid waste pretreatment unit; 2, anaerobic digestion unit; and 3, residue collection tank.

II, biogas measurement and collection unit; where 4, gas flow meter; and 5, high-pressure biogas collection device; and III, methane purification and liquefaction unit; where 6, high-pressure separation tank; 7, liquefaction pretreatment device; 8, heavy hydrocarbon and benzene removal device; 9, two-stage rectification device; 10, low-temperature pressure liquid storage tank; and 11, buffer storage tank.

DETAILED DESCRIPTION OF EMBODIMENTS

The technical solutions in the embodiments will be clearly and completely described below with reference to the embodiments of the present application. Obviously, the embodiments described herein are only a part of the embodiments, rather than all the embodiments of the present application. Any other embodiments made by those skilled in the art based on the embodiments of the present application without sparing any creative efforts shall fall within the scope of the present application.

In addition, for the purpose of illustration, a lot of specific details are given in the following embodiments. It should be understood for those skilled in the art that the present application can also be implemented with only a part of the specific details given herein. In some embodiments, the methods and means well-known to those skilled in the art are not described in detail, which is intended to highlight the spirit of the present application. All the units of the raw material content of the present application are based on parts by weight, unless otherwise specified. In addition, the technical indicators in the present application are measured by standard methods used in the field, which can refer to latest national standards in details, unless otherwise specified.

It should be understood that terms such as "have", "comprise" and "include" used herein do not exclude the presence or addition of one or more other elements or combinations thereof.

In a first aspect, the present application provides a system for high-value utilization of organic solid waste, which includes an anaerobic digestion unit, a biogas measurement and collection unit and a methane purification and liquefaction unit.

The anaerobic digestion unit includes an organic solid waste pretreatment device, an anaerobic digestion device and a residue collection tank which are connected in sequence.

The biogas measurement and collection unit includes a gas flow meter and a high-pressure biogas collection device which are connected in sequence.

The methane purification and liquefaction unit includes a high-pressure separation tank, a liquefaction pretreatment device, a heavy hydrocarbon and benzene removal device, a two-stage rectification device and a low-temperature pressure liquid storage tank which are connected in sequence. The two-stage rectification device is also connected to a buffer storage tank. The buffer storage tank and the low-temperature pressure liquid storage tank are connected.

A gas outlet of the anaerobic digestion device is communicated with a gas inlet of the gas flow meter.

A gas outlet of the high-pressure biogas collection device is communicated with a gas inlet of the high-pressure separation tank.

A liquid outlet of the high-pressure separation tank is connected to a liquid inlet of the two-stage rectification device.

In an embodiment, the anaerobic digestion device includes an anaerobic digestion tank, a heating device and a stirring device. The stirring device is provided in a center of an interior of the anaerobic digestion tank. An outside of the anaerobic digestion tank is surrounded by the heating device. A top of the anaerobic digestion tank is provided with a biogas outlet, a solid material inlet, an acid liquor inlet, an alkali liquor inlet, a pH or temperature detector and a stirring motor. A bottom of the anaerobic digestion tank is provided with a discharge port.

In an embodiment, the heating device is a water-bath heater, a coil heater or a combination thereof.

In an embodiment, the stirring device is selected from at least one of a center shaft mixer, a horizontal mixer, an inclined mixer and a submersible mixer.

In an embodiment, the two-stage rectification device includes a first-stage rectification tower, a two-stage rectification tower, a main heat exchanger, a supercooler, a tower kettle and a tower overhead device which are connected. Their connection manner is similar to that in the existing two-stage rectification process for producing high-purity methane.

In a second aspect, the present application provides a method for high-value utilization of the organic solid waste using the system mentioned above. The method includes the following steps.

The organic solid waste is pretreated by the organic solid waste pretreatment device to obtain a digestion material. Then, anaerobic digestion processes after the digestion material enters the anaerobic digestion device. A biodegradable organic matter in the organic solid waste generates monomers (including monosaccharides, a small amount of amino acids and high fatty acids) under the action of hydrolysis bacteria. The monomers are used to generate an intermediate product, i.e., a volatile organic acid, under the action of acidifying bacteria in the acid production process. In the subsequent process of hydrogen production and acetic acid production, gases (including $CH_4$, $H_2$, $CO_2$ and $N_2$), acetic acid, methylamine and the like are generated. Next, under the action of methanogens, anaerobic digestion products (including digestion residues and biogas) are generated. The biogas generated in the anaerobic digestion unit flows into the gas flow meter of the biogas measurement and collection unit and is converted into a high-pressure raw gas by the high-pressure biogas collection device. The obtained high-pressure raw gas is sent to the high-pressure separation tank to carry out liquid separation treatment to obtain a condensed liquid. The obtained condensed liquid enters into a two-stage rectification system. The high-pressure raw gas enters the liquefaction pretreatment device for desulfurization, dehydration and $CO_2$ removal, and then enters the heavy hydrocarbon and benzene removal device to remove heavy hydrocarbons and trace benzene, and then passes through the two-stage rectification device to generate liquid methane, which is stored in low-temperature pressure liquid storage tank. A small amount of a surplus liquid that undergoes supercooling is discharged into the buffer storage tank for accumulation, and the surplus liquid accumulated to a certain amount is taken out and sent into the low-temperature pressure liquid storage tank.

The non-biodegradable organic matter in the organic solid waste becomes digestion residue through anaerobic digestion and enters a residue collection tank for recycling.

In an embodiment, the digestion material stays in the anaerobic digestion device for 20-40 days.

In an embodiment, a temperature of the anaerobic digestion device ranges within 35-39° C., 41-45° C., or 53-57° C. for biogas production.

In an embodiment, after a pressure of biogas collected in the high-pressure biogas collection device reaches 120 bar at 27° C., the biogas enters the high-pressure separation tank.

In an embodiment, in the liquefaction pretreatment device, $CO_2$ removal, desulfurization and dehydration are carried out. The dehydration is performed after the $CO_2$ removal. The $CO_2$ removal and the desulfurization are simultaneously performed. $CO_2$ is removed by ethanolamine (MEA) through absorption. The dehydration is performed using a molecular sieve dehydration method for further removing sulfide.

In an embodiment, the organic solid waste is one or more combinations of domestic, agricultural and industrial waste.

In an embodiment, the domestic waste may be originated from urban sludge, household garbage, garden waste, etc. The agricultural waste may be originated from agricultural straw, mulching film, livestock and poultry manure, etc. The industrial waste may be originated from oil sludge, bacterial residue, industrial organic solid waste, etc.

Embodiment 1

1000 kg organic solid waste is originated from municipal sludge.

The process of high-value utilization of the organic solid waste is described as follows. In the organic solid waste pretreatment system, the organic solid waste is hydrolyzed for 20 min at a temperature of 165-180° C. and a pressure of 1 MPa to obtain the digestion material. The digestion material enters the anaerobic digestion unit to carry out anaerobic digestion for 30 days at a temperature of 35-39° C. to generate biogas. The obtained biogas with 300-500 m³ flows into the gas flow meter of the biogas measurement and collection unit. The biogas becomes the high pressure raw gas by the biogas high pressure collection device to have a pressure of 120 bar at 27° C. The obtained high-pressure raw gas is sent to the high-pressure separation tank of the methane purification and liquefaction unit to carry out liquid separation treatment to obtain a condensed liquid. The obtained condensed liquid enters into a two-stage rectification system. The high-pressure raw gas enters the liquefaction pretreatment system for desulfurization, dehydration and $CO_2$ removal. Specifically, the dehydration is performed after the $CO_2$ removal. The $CO_2$ removal and the desulfurization are simultaneously performed. $CO_2$ is removed by ethanolamine (MEA) through absorption. The dehydration is performed using a molecular sieve dehydration method for further removing sulfide. Next, the high-pressure raw gas enters the heavy hydrocarbon and benzene removal device to remove heavy hydrocarbons and trace benzene, and then passes through the two-stage rectification device to generate liquid methane, which is stored in low-temperature pressure liquid storage tank. A small amount of a surplus liquid that undergoes supercooling is discharged into the buffer storage tank.

The non-biodegradable organic matter in the organic solid waste becomes digestion residue through anaerobic digestion and enters a residue collection tank for recycling.

Finally, 200-300 kg liquid methane is produced. After testing, the purity of the obtained liquid methane is 99.9%, which can meet the demand of a liquid oxygen methane engine for methane fuel.

Embodiment 2

The present embodiment differs from Embodiment 1 in that in the present embodiment, the anaerobic digestion processes for 30 days at a temperature of 53-57° C. Finally, 300-500 kg liquid methane is produced. After testing, the purity of the obtained liquid methane is 99.9%, which can meet the demand of a liquid oxygen methane engine for methane fuel.

Embodiment 3

The present embodiment differs from Embodiment 1 in that the 1000 kg organic solid waste is originated from kitchen waste. In the organic solid waste pretreatment system, the organic solid waste is crushed and then hydrolyzed for 2 h at a temperature of 110-130° C. and a pressure of 1 MPa. Anaerobic digestion processes for 30 days at a temperature of 35-39° C. Finally, 550-650 kg liquid methane is produced. After testing, the purity of the obtained liquid methane is 99.9%, which can meet the demand of a liquid oxygen methane engine for methane fuel.

Embodiment 4

The present embodiment differs from Embodiment 1 in that the organic solid waste is originated from agricultural straw. In the organic solid waste pretreatment system, the organic solid waste is crushed and then hydrolyzed for 10 min at a temperature of 160-270° C. and a pressure of 2 MPa. Anaerobic digestion processes for 30 days at a temperature of 53-57° C. Finally, 600-700 kg liquid methane is produced. After testing, the purity of the obtained liquid methane is 99.9%, which can meet the demand of a liquid oxygen methane engine for methane fuel.

Embodiment 5

The present embodiment differs from Embodiment 1 in that the organic solid waste is originated from oil sludge. In the organic solid waste pretreatment system, the organic solid waste is crushed and then hydrolyzed for 30 min at a temperature of 160-200° C. and a pressure of 1 MPa. Anaerobic digestion processes for 30 days at a temperature of 41-45° C. Finally, 300-400 kg liquid methane is produced. After testing, the purity of the obtained liquid methane is 99.9%, which can meet the demand of a liquid oxygen methane engine for methane fuel.

What is claimed is:

1. A system for utilization of organic solid waste, comprising:
   an anaerobic digestion unit;
   a biogas measurement and collection unit; and
   a methane purification and liquefaction unit;
   wherein the anaerobic digestion unit comprises an organic solid waste pretreatment device, an anaerobic digestion device and a residue collection tank which are connected in sequence;
   the biogas measurement and collection unit comprises a gas flow meter and a biogas collection device which are connected in sequence;
   the methane purification and liquefaction unit comprises a separation tank, a liquefaction pretreatment device, a heavy hydrocarbon and benzene removal device, a two-stage rectification device and a liquid storage tank which are connected in sequence, wherein the two-stage rectification device is also connected to a buffer storage tank; and the buffer storage tank and the liquid storage tank are connected;
   a gas outlet of the anaerobic digestion device is communicated with a gas inlet of the gas flow meter;
   a gas outlet of the biogas collection device is communicated with a gas inlet of the separation tank;

a liquid outlet of the separation tank is connected to a liquid inlet of the two-stage rectification device;

the two-stage rectification device comprises a first-stage rectification tower, a second-stage rectification tower, a main heat exchanger, a supercooler, a tower kettle and a tower overhead device; and an ethanolamine absorption device and a dehydration device are provided in the liquefaction pretreatment device.

2. The system of claim 1, wherein the anaerobic digestion device comprises an anaerobic digestion tank, a heating device and a stirring device; the stirring device is provided in a center of an interior of the anaerobic digestion tank; an outside of the anaerobic digestion tank is surrounded by the heating device; a top of the anaerobic digestion tank is provided with a biogas outlet, a solid material inlet, an acid liquor inlet, an alkali liquor inlet, a pH or temperature detector and a stirring motor; and a bottom of the anaerobic digestion tank is provided with a discharge port;

the heating device is a water-bath heater, a coil heater or a combination thereof; and the stirring device is selected from at least one of a center shaft mixer, a horizontal mixer, an inclined mixer and a submersible mixer.

* * * * *